United States Patent
Fang et al.

(10) Patent No.: US 7,846,479 B2
(45) Date of Patent: Dec. 7, 2010

(54) MICROPARTICLE COMPOSITIONS AND METHODS FOR THE MANUFACTURE THEREOF

(75) Inventors: Jia-Hwa Fang, Oakland, CA (US); Manmohan Singh, Hercules, CA (US); Derek O'Hagan, Berkeley, CA (US); Maninder Hora, Danville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/775,964

(22) Filed: Feb. 10, 2004

(65) Prior Publication Data

US 2004/0156913 A1    Aug. 12, 2004

Related U.S. Application Data

(62) Division of application No. 09/967,462, filed on Sep. 28, 2001, now Pat. No. 6,753,015.

(60) Provisional application No. 60/236,077, filed on Sep. 28, 2000.

(51) Int. Cl.
    *A61K 9/14* (2006.01)
(52) U.S. Cl. ............... 424/489; 424/484; 424/486
(58) Field of Classification Search ............ 424/489, 424/484, 486
    See application file for complete search history.

(56) References Cited

U.S. PATENT DOCUMENTS

| | | | |
|---|---|---|---|
| 3,523,907 A | 8/1970 | Vrancken et al. | 252/316 |
| 5,538,739 A | 7/1996 | Bodmer et al. | 424/501 |
| 5,643,605 A | 7/1997 | Cleland et al. | 424/489 |
| 5,783,567 A | 7/1998 | Hedley et al. | 514/44 |
| 5,814,482 A | 9/1998 | Dubensky, Jr. et al. | 435/69.3 |
| 5,840,970 A * | 11/1998 | Sumner et al. | 562/487 |
| 5,842,723 A | 12/1998 | Hartling et al. | 285/49 |

(Continued)

FOREIGN PATENT DOCUMENTS

WO        WO 90/14837        12/1990

(Continued)

OTHER PUBLICATIONS

Singh et al. (Cationic microparticles: A potent delivery system for DNA vaccines in PNAS, vol. 97, No. 2, Jan. 2000, pp. 811-816.*

(Continued)

*Primary Examiner*—Blessing M Fubara
(74) *Attorney, Agent, or Firm*—Helen Lee; David Bonham

(57) ABSTRACT

Microparticles with adsorbed complexes of macromolecule and detergent, methods of making such microparticles, and uses thereof, are disclosed. The microparticles comprise a polymer, such as a poly($\alpha$-hydroxy acid), a polyhydroxy butyric acid, a polycaprolactone, a polyorthoester, a polyanhydride, and the like, and are formed using cationic, anionic, or nonionic detergents. The surfaces of the microparticles have adsorbed thereon a complex of biologically active macromolecules, such as nucleic acids, polypeptides, antigens, and adjuvants, and a detergent. Preferred polymers are poly (D,L-lactide-co-glycolides), more preferably those having a lactide/glycolide molar ratio ranging from 40:60 to 60:40 and having a molecular weight ranging from 30,000 Daltons to 70,000 Daltons. Preferred macromolecules are bacterial and viral antigens (such as HIV antigens, meningitis B antigens, streptococcus B antigens, and Influenza A hemagglutinin antigens) as well as polynucleotides that encode for such antigens.

23 Claims, 1 Drawing Sheet

U.S. PATENT DOCUMENTS

| | | | |
|---|---|---|---|
| 5,869,103 A | 2/1999 | Yeh et al. | 424/501 |
| 5,871,747 A | 2/1999 | Gengoux-Sedlik et al. | 424/208.1 |
| 5,928,647 A | 7/1999 | Rock | 424/196.11 |
| 6,015,686 A | 1/2000 | Dubensky, Jr. et al. | 435/69.1 |
| 6,086,901 A * | 7/2000 | O'Hagan et al. | 424/283.1 |
| 6,395,253 B2 * | 5/2002 | Levy et al. | 424/1.25 |
| 6,562,346 B1 * | 5/2003 | Paliard et al. | 424/189.1 |
| 2001/0046967 A1 * | 11/2001 | Van Nest | 514/44 |
| 2002/0009466 A1 | 1/2002 | Brayden | 424/252.1 |

FOREIGN PATENT DOCUMENTS

| | | | |
|---|---|---|---|
| WO | WO 94/15635 | | 7/1994 |
| WO | WO 94/28879 | | 12/1994 |
| WO | WO 95/24929 | | 9/1995 |
| WO | WO-95/24929 | * | 9/1995 |
| WO | WO 96/20698 | | 7/1996 |
| WO | WO 97/02810 | | 1/1997 |
| WO | WO 97/38087 | | 10/1997 |
| WO | WO 98/10750 | | 3/1998 |
| WO | WO 98/33487 | | 8/1998 |
| WO | WO 99/18226 | | 4/1999 |
| WO | WO 00/06123 | | 2/2000 |
| WO | WO 00/50006 | * | 8/2000 |
| WO | WO 01/81609 A2 | | 1/2001 |
| WO | WO 01/36599 | | 5/2001 |

OTHER PUBLICATIONS

Kazzaz, J. et al., "Induction of Cytotoxic T-lymphocyte activity in mice with HIV p24 gag protein adsorbed to the surface of poly(lactide-co-glycolide) microparticles," Proceed. Int'l Symp. Control. Rel. Bioact. Mater., 26 (1999), Controlled Release Society, pp. 104-105.

Coombes, A.G.A. et al., "Single Does, Polymeric, Microparticle-Based Vaccines: The Influence of Formulation Conditions on the Magnitude and Duration of the Immune Response to a Protein Antigen," Vaccine, vol. 14, No. 15, 1996, pp. 1429-1438.

Duncan, J.D. et al., "Poly(lactide-co-glycolide) Microencapsulation of Vaccines for Mucosal Immunization," Mucosal Vaccines, 1996, pp. 159-173.

Eldridge, J. et al., "New Advances in Vaccine Delivery Systems," Seminars in Hemotology, vol. 30, No. 4, Suppl. 4, Oct. 1993, pp. 16-25.

Higgins, D. et al., "MF59 Adjuvant Enhances the Immunogenicity of Influenza Vaccine in Both Young and Old Mice," Vaccine, vol. 14, No. 6, 1996, pp. 478-484.

Men, Y. et al., "Introduction of a Cytotoxic T Lymphocite Response by Immunization With a Malaria Specific CTL Peptide Entrapped in Biodegradable Polymer Microspheres," Vaccine, vol. 15, No. 12/13, 1997, pp. 1405-1412.

Moore, A. et al., "Immunization With a Soluble Recombinant HIV Protein Entrapped in Biodegradable Microparticles Induces HIV-Specific CD8+ Cytotoxic T Lymphocites and CD4+ TH1 Cells," Vaccine, vol. 13, No. 18, 1995, pp. 1741-1995.

Nakaoka, R. et al., "Enhanced Antibody Production Through Sustained Antigen Release From Biodegradable Granules," Journal of Controlled Release, vol. 37 (1995), pp. 215-224.

O'Hagan, Derek et al., Biodegradable Microparticles for Oral Immunization, Vaccine, vol. 11, 1993, pp. 149-154.

O'Hagan, Derek et al., "Long-Term Antibody Responses in Mice Following Subcutaneous Immunization With Ovalbumin Entrapped in Biodegradable Microparticles," Vaccine, vol. 11, 1993, pp. 1965-1969.

Sah, H. et al., "Continuous Release of Proteins From Biodegradable Microcapsules and in Vivo Evaluation of Their Potential as a Vaccine Adjuvant," Journal of Controlled Release 35 (1995), pp. 137-144.

Vordermeier, H.M. et al., "Synthetic Delivery System for Tuberculosis Vaccines: Immunological Evaluation of the M. Tuberculosis 38 kDa Protein Entrapped in Biodegradable PLG Microparticles," Vaccine, vol. 13, No. 16, 1995, pp. 1576-1582.

Powell, M. F. et al., "Vaccine Design: The Subunit and Adjuvant Approach," Plenum Press, New York, 1995, p. 183.

Eldridge, J. et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," Infection and Immunity, vol. 59, No. 9, Sep. 1991, pp. 2978-2986.

Singh, Manmohan et al., "The preparation and characterization of polymeric antigen delivery systems for oral administration," Advanced Drug Delivery Reviews 34 (1998), pp. 285-304.

Denis-Mize, K.S. et al., "Plasmid DNA Adsorbed onto cationic microparticles mediates target gene expression and antigen presentation by dendritic cells," Gene Therapy 2000, pp. 2105-2112.

Kazzaz, J. et al., "Novel anionic microparticles are a potent adjuvant for the induction of cytotoxic T lymphocytes against recombinant p55 from HIV-1," Journal of Controlled Release 67 (2000), pp. 347-356.

Singh, Manmohan et al., "Cationic microparticles: A potent delivery system for DNA vaccines," Proceedings of the National Academy of Science, Jan. 18, 2000, vol. 97, No. 2, pp. 811-816.

O'Hagan, Derek T., et al., "Long-term antibody responses in mice following subcutaneous immunization with ovalbumin entrapped in biodegradable microparticles," Vaccine, vol. 11, Issue 9, 1993, pp. 965-969.

Hayley, Jeffery et al., "The preparation and Characterization of Poly(lactide-co-glycolide) Microparticles. II. The Entrapment of a Model Protein Using a (Water-in-Oil)-in-Water Emulsion Solvent Eaporation Technique," Pharmaceutical Research, vol. 10, No. 3, 1993, pp. 362-368.

Ogawa, Yasuaki et al., "A New Technique to Efficiently Entrap Leuprolide Acetate Into Microcapsules of Polylactic Acid or Copoly (Lactic/Glycolic) Acid," Chem. Pharm. Bull., vol. 36, 1988, pp. 1095-1103.

Polo, John M. et al., "Stable alphavirus packaging cell lines for Sindbis virus-and Semliki Forest virus-derived vectors," Proceedings of the National Academy of Science, vol. 96, Apr. 1999, pp. 4598-4603.

Chapman, Barbara S., "effect of intron A from human cytomegalovirus (Towne) immediate-early gene on heterologous expression in mammalian cells," Nucleic Acids Research, vol. 19, No. 14, pp. 3979-3986.

Elias Fattal et al., "Biodegradable polyalkylcyanoacrylate nanoparticles for the delivery of oligonucleotides", Journal of Controlled Release, 53, 1998, pp. 137-143.

Christine Chavany et al, "Polyalkylcyanoacrylate Nanoparticles as Polymeric Carriers for Antisense Oligonucleotides", Pharm. Res., vol. 9, No. 4, 1992, pp. 441-449.

* cited by examiner

US 7,846,479 B2

MICROPARTICLE COMPOSITIONS AND METHODS FOR THE MANUFACTURE THEREOF

STATEMENT OF RELATED APPLICATION

This application is a divisional application of co-pending U.S. Patent application Ser. No. 09/967,462, filed Sep. 28, 2001, entitled "Microparticle Compositions and Methods For the Manufacture Thereof," which claims the benefit of U.S. Provisional Patent Application Ser. No. 60/236,077, filed Sep. 28, 2000, which is incorporated herein by reference in its entirety.

TECHNICAL FIELD

The present invention relates generally to pharmaceutical compositions. In particular, the invention relates to microparticles with adsorbent surfaces, methods for preparing such microparticles, and uses thereof. Additionally, the invention relates to compositions comprising biodegradable microparticles wherein biologically active agents, such as therapeutic polynucleotides, polypeptides, antigens, and adjuvants, are adsorbed on the surface of the microparticles.

BACKGROUND

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919), poly (lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable while PLG particles biodegrade by random nonenzymatic hydrolysis of ester bonds to lactic and glycolic acids, which are excreted along normal metabolic pathways.

For example, U.S. Pat. No. 5,648,095 describes the use of microspheres with encapsulated pharmaceuticals as drug delivery systems for nasal, oral, pulmonary and oral delivery. Slow-release formulations containing various polypeptide growth factors have also been described. See, e.g., International Publication No. WO 94/12158, U.S. Pat. No. 5,134,122 and International Publication No. WO 96/37216.

Fattal et al., Journal of Controlled Release 53:137-143 (1998) describes nanoparticles prepared from polyalkylcyanoacrylates (PACA) having adsorbed oligonucleotides.

Particulate carriers have also been used with adsorbed or entrapped antigens in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. For example, commonly owned, co-pending application Ser. No. 09/015,652, filed Jan. 29, 1998, describes the use of antigen-adsorbed and antigen-encapsulated microparticles to stimulate cell-mediated immunological responses, as well as methods of making the microparticles.

In commonly owned co-pending U.S. patent application Ser. No. 09/015,652 filed Jan. 29, 1998, for example, a method of forming microparticles is disclosed which comprises combining a polymer with an organic solvent, then adding an emulsion stabilizer, such as the surfactant polyvinyl alcohol (PVA), then evaporating the organic solvent, thereby forming microparticles. The surface of the microparticles comprises the polymer and the stabilizer. Macromolecules such as DNA, polypeptides, and antigens may then be adsorbed on those surfaces.

U.S. Pat. Nos. 5,814,482 and 6,015,686 disclose Eukaryotic Layered Vector Initiation Systems (ELVIS vectors), particularly those derived and constructed from alphavirus genomes (such as Sindbis virus), for use in stimulating an immune response to an antigen, in methods of inhibiting pathogenic agents, and in delivery of heterologous nucleotide sequences to eukaryotic cells and animals, among others.

Commonly owned International patent application PCT/US99/17308 and co-pending U.S. patent application Ser. No. 09/715,902 disclose methods of making microparticles having adsorbed macromolecules, such as a pharmaceutical, a polynucleotide, a polypeptide, a protein, a hormone, an enzyme, a transcription or translation mediator, an intermediate in a metabolic pathway, an immunomodulator, an antigen, an adjuvant, or combinations thereof, and the like. The microparticles comprise, for example, a polymer such as a poly(alpha-hydroxy acid) (e.g., PLG), a polyhydroxy butyric acid, a polycaprolactone, a polyorthoester, a polyanhydride, and the like, and are formed using, for example, cationic, anionic or nonionic detergents.

While antigen-adsorbed PLG microparticles offer significant advantages over other more toxic systems, adsorption of biologically active agents to the microparticle surface can nonetheless be improved. For example, it is often difficult or impossible to adsorb charged or bulky biologically active agents, such as polynucleotides, large polypeptides, and the like, to the microparticle surface. Thus, there is a continued need for flexible delivery systems for such agents and, particularly for drugs that are highly sensitive and difficult to formulate.

SUMMARY OF THE INVENTION

The present inventors have found that adsorption of macromolecules to microparticles can be improved by ensuring that detergent is made available for forming a complex with the macromolecules at the time of adsorption. This availability can be accomplished, for example, by separately providing a quantity of detergent at the time of macromolecule adsorption or by ensuring that the process for producing the microparticles results in a product containing a substantial amount of unbound detergent. This provision is to be contrasted with prior art techniques, where microparticles are thoroughly washed to remove residual detergent prior to macromolecule adsorption. For instance, in the Examples found in PCT/US99/17308 above, the microparticles are washed multiple times with water (i.e., they are washed with water four times by centrifugation) prior to exposure to the macromolecule of interest. Such washing steps remove essentially all unbound detergent, resulting in a final product in which greater than 99% of the remaining detergent is bound to the particles.

Thus, according to a first aspect of the invention, a microparticle composition is provided which comprises: (1) microparticles, which further comprise a polymer and a first detergent portion that is bound to the polymer; and (2) a complex of a biologically active macromolecule with a second detergent portion, which complex is adsorbed on the surface of the microparticles. The first detergent portion and the second detergent portion can comprise the same detergent or different detergents.

Preferred biologically active macromolecules are selected from the group consisting of a polypeptide, a polynucleotide, a polynucleoside, an antigen, a pharmaceutical, a hormone, an enzyme, a transcription or translation mediator, an intermediate in a metabolic pathway, an immunomodulator, and an adjuvant. Preferred polymers are poly(α-hydroxy acids), more preferably those selected from the group consisting of poly(L-lactide), poly(D,L-lactide) and poly(D,L-lactide-co-glycolide). More preferred are poly(D,L-lactide-co-glycolide) polymers. Preferred poly(D,L-lactide-co-glycolide) polymers are those having a lactide/glycolide molar ratio ranging from 30:70 to 70:30, more preferably 40:60 to 60:40, and having a molecular weight ranging from 10,000 to 100,000 Daltons, more preferably from 30,000 Daltons to 70,000 Daltons. More preferred biologically active macromolecules include bacterial and viral antigens (e.g., HIV antigens such as gp120, gp140, p24gag and p55gag, meningitis B antigens, streptococcus B antigens, and Influenza A hemagglutinin antigens) and polynucleotides that encode for antigens. The biologically active macromolecule can be, for example, in the form of a plasmid, an ELVIS vector, or an RNA vector construct. A particularly preferred biologically active macromolecule is pCMV-p55gag.

In some embodiments, the microparticle composition is provided with a further biologically active macromolecule, which may be bound or unbound, and may even be entrapped within the polymer. For example, the microparticle composition may be provided with an adjuvant, particularly a Th1 stimulating adjuvant. Preferred adjuvants include CpG oligonucleotides, LTK63, LTR72, MPL and aluminum salts, including aluminum phosphate.

In some embodiments, the first detergent portion and the second detergent portion comprise the same detergent. Preferred detergents for this purpose are cationic detergents, for example, CTAB. In such embodiments, the first detergent portion (which is bound to the polymer) preferably comprises about 5-95% of the total detergent in the composition, more preferably about 10-90%, even more preferably about 10-60%, and most preferably about 25-40%.

In other embodiments, the first detergent portion and the second detergent portion comprise different detergents. For example, the first detergent portion can comprise a nonionic detergent (e.g., PVA) and the second detergent portion can comprise a cationic detergent (e.g., CTAB).

According to another aspect of the presenting invention, a pharmaceutically acceptable excipient is added to the above microparticle compositions.

Another aspect of the invention is directed to the delivery of a macromolecule to a vertebrate subject, which comprises administering to a vertebrate subject the microparticle composition above.

In an additional aspect, the invention is directed to a method for eliciting a cellular and/or humoral immune response in a vertebrate subject, which comprises administering to a vertebrate subject a therapeutically effective amount of a microparticle composition as described above.

Another aspect of the invention is directed to a method of immunization, which comprises administering to a vertebrate subject a therapeutically effective amount of the microparticle composition above.

In other aspects of the invention, the above microparticle compositions are used in the diagnosis of diseases, in the treatment of diseases, in vaccines, and/or in raising an immune response.

Still other aspects of the invention are directed to methods of producing microparticle compositions. In general, these methods comprise: (a) forming an emulsion comprising (i) a polymer selected from the group consisting of a poly(α-hydroxy acid), a polyhydroxy butyric acid, a polycaprolactone, a polyorthoester, a polyanhydride, and a polycyanoacrylate, (ii) an organic solvent, (iii) a detergent and (iv) water; followed by (b) removal of the organic solvent. About 10-90% of the total detergent in the resulting composition is preferably bound to microparticles in this embodiment, more preferably about 10-60%, and most preferably about 25-40%. In general, these microparticle compositions are subsequently incubated with a biologically active macromolecule, such as those discussed above, to produce a biologically active composition.

Preferably the emulsion is a water-in-oil-in-water emulsion that is formed by a process comprising: (a) emulsifying an organic phase comprising the polymer and the organic solvent with a first aqueous phase comprising water to form a water-in-oil emulsion; and (b) emulsifying a second aqueous phase comprising the cationic detergent and water with the emulsion formed in step (a) to form a water-in-oil-in-water emulsion.

In some preferred embodiments, the detergent is a cationic detergent, which is provided in the emulsion at a weight to weight detergent to polymer ratio of from about 0.05:1 to about 0.5:1. In these embodiments, the method preferably further comprises cross-flow filtration of the particles after the solvent removal step. In a specific embodiment, the polymer is poly(D,L-lactide-co-glycolide), the cationic detergent is CTAB, and the cationic detergent is provided in the emulsion at a weight to weight detergent to polymer ratio of from about 0.1:1 to about 0.5:1.

In other preferred embodiments, the detergent is a cationic detergent that is provided in the emulsion at a weight to weight detergent to polymer ratio of from about 0.001:1 to about 0.05:1. At these lower levels, there is typically no need for a filtration or washing step to remove excess detergent. In a specific embodiment, the cationic detergent is CTAB, the polymer is poly(D,L-lactide-co-glycolide), the cationic detergent is provided in the emulsion at a weight to weight detergent to polymer ratio of from about 0.002:1 to about 0.04:1, and the microparticles are not subjected to a step to remove excess CTAB from the composition.

Still other aspects of the invention are directed to methods of producing microparticle compositions, which methods comprise: (1) providing a microparticle in an emulsification process, which microparticle comprises a polymer and a first detergent portion that is bound to the microparticle; and (2) adsorbing a complex of a biologically active macromolecule and a second detergent portion on the surface of the microparticle. The first detergent portion and the second detergent portion can comprise the same detergent or different detergents. The polymer is preferably selected from the group consisting of a poly(α-hydroxy acid), a polyhydroxy butyric acid, a polycaprolactone, a polyorthoester, a polyanhydride, and a polycyanoacrylate.

In some embodiments, the first and second detergent portions comprise the same detergent. The detergent is preferably a cationic detergent, for example, CTAB. In these embodiments, about 10-90%, more preferably about 10-60%, and most preferably about 25-40% of the total detergent in the microparticle composition is in the form of the first detergent portion that is bound to the microparticles. Typically, all of the detergent is added during the course of the emulsification process.

In other embodiments, the first detergent portion comprises a first detergent and the second detergent portion comprises a second detergent differing from the first detergent. Typically, the first detergent is added in the course of the emulsification process and the second detergent is added subsequent to the emulsification process, preferably concurrently with the biologically active macromolecule. Preferably the first detergent portion comprises a nonionic detergent, such as PVA, and the second detergent portion comprises a cationic detergent, such as CTAB.

These and other embodiments of the present invention will readily occur to those of ordinary skill in the art in view of the disclosure herein.

DETAILED DESCRIPTION OF THE INVENTION

Figure 1:
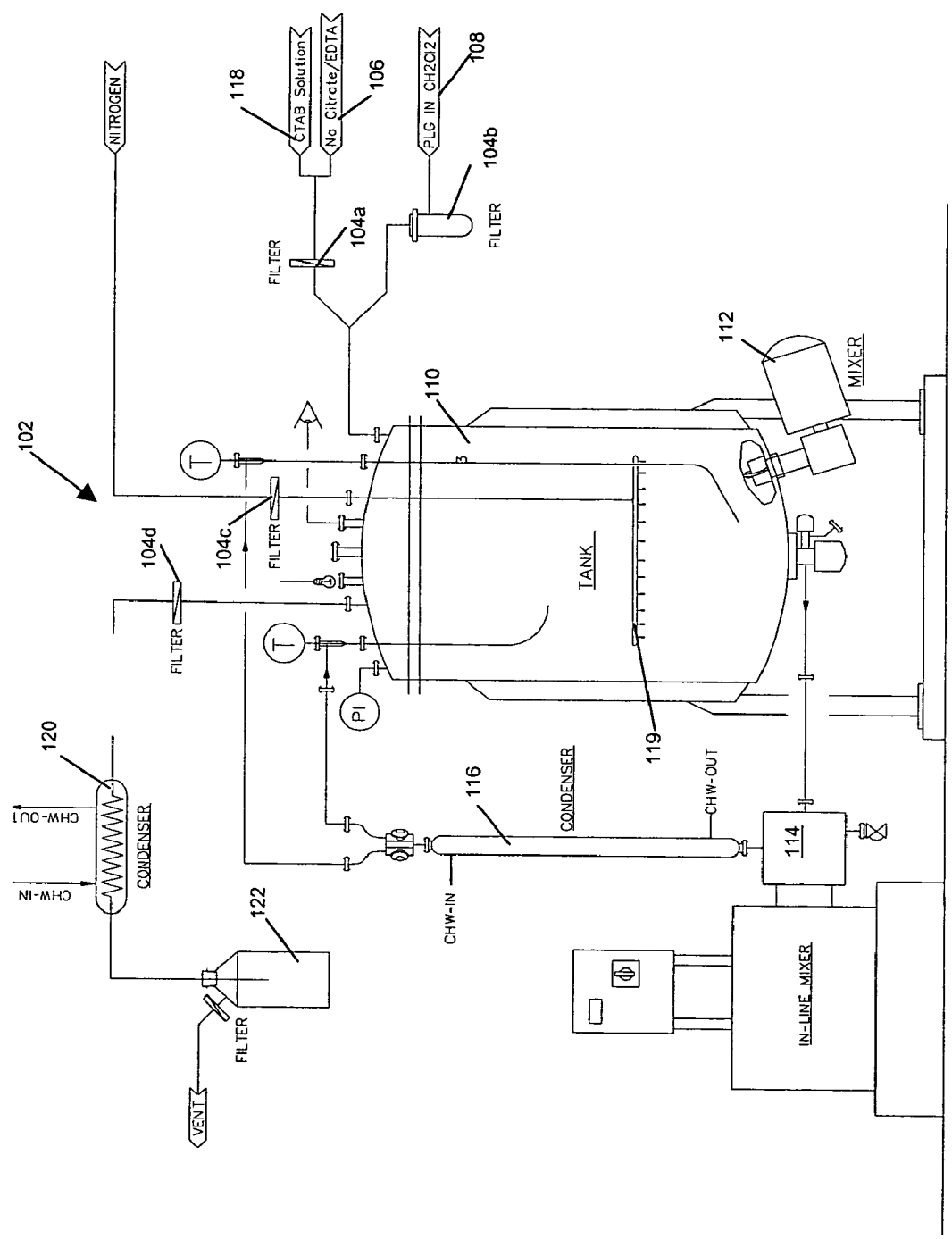
FIG. 1 is a schematic diagram of an apparatus appropriate for producing the microparticles of the present invention.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher's Polymer Chemistry* (4th edition, Marcel Dekker Inc., 1996).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, the term "microparticle" refers to one or more microparticles, and the like.

A. DEFINITIONS

In describing the present invention, the following terms will be employed, and are intended to be defined as indicated below.

Unless stated otherwise, all percentages and ratios herein are given on a weight basis.

The term "microparticle" as used herein, refers to a particle of about 10 nm to about 150 μm in diameter, more preferably about 200 nm to about 30 μm in diameter, and most preferably about 500 nm to about 10 μm in diameter. Preferably, the microparticle will be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Polymer microparticles for use herein are formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are polymer microparticles derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The polymer microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

The term "detergent" as used herein includes surfactants, dispersing agents, suspending agents, and emulsion stabilizers. Anionic detergents include, but are not limited to, SDS (sodium dodecyl sulfate), SLS (sodium lauryl sulfate), DSS (disulfosuccinate), sulphated fatty alcohols, and the like. Cationic detergents include, but are not limited to, cetrimide (cetyl trimethyl ammonium bromide, or "CTAB"), benzalkonium chloride, DDA (dimethyl dioctodecyl ammonium bromide), DOTAP (dioleoyl-3-trimethylammonium-propane), and the like. Nonionic detergents include, but are not limited to, nonionic surfactants such as PVA, povidone (also known as polyvinylpyrrolidone or PVP), sorbitan esters, polysorbates, polyoxyethylated glycol monoethers, polyoxyethylated alkyl phenols, poloxamers, and the like.

After microparticle formation, the detergent may be bound or unbound to the same. Where bound, the detergent can be attached to the microparticles by any mechanism including, but not limited to, ionic bonding, hydrogen bonding, covalent bonding, physical entrapment, Van der Waals bonding, and bonding through hydrophilic/hydrophobic interactions.

The term "macromolecule" as used herein refers to, without limitation, a pharmaceutical, a polynucleotide, a polypeptide, a hormone, an enzyme, a transcription or translation mediator, an intermediate in a metabolic pathway, an immunomodulator, an antigen, an adjuvant, or combinations thereof. Particular macromolecules for use with the present invention are described in more detail below. A "complexed" macromolecule is a macromolecule which has formed an association with a detergent and which is then amenable to adsorption to a microparticle.

The term "pharmaceutical" refers to biologically active compounds such as antibiotics, antiviral agents, growth factors, hormones, and the like, discussed in more detail below.

The term "adjuvant" refers to any substance that assists or modifies the action of a pharmaceutical, including but not limited to immunological adjuvants, which increase or diversify the immune response to an antigen.

A "polynucleotide" is a nucleic acid polymer, which typically encodes a biologically active (e.g., immunogenic or therapeutic) protein or polypeptide. Depending on the nature of the polypeptide encoded by the polynucleotide, a polynucleotide can include as little as 10 nucleotides, e.g., where the polynucleotide encodes an antigen. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and especially synthetic DNA sequences. The term also captures sequences that include any of the known base analogs of DNA and RNA. The term further includes modifications, such as deletions, additions and substitutions (generally conservative in nature), to a native sequence, preferably such that the nucleic acid molecule encodes a therapeutic or antigenic protein. These modifications may be deliberate, as through site-directed mutagenesis, or may be accidental, such as through mutations of hosts which produce the antigens.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, preferably such that the protein maintains the ability to elicit an immunological response or have a therapeutic effect on a subject to which the protein is administered.

By "antigen" is meant a molecule which contains one or more epitopes capable of stimulating a host's immune system to make a cellular antigen-specific immune response when the antigen is presented in accordance with the present invention, or a humoral antibody response. An antigen may be capable of eliciting a cellular or humoral response by itself or when present in combination with another molecule. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Nati. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols, supra.*

The term "antigen" as used herein denotes both subunit antigens, i.e., antigens which are separate and discrete from a whole organism with which the antigen is associated in nature, as well as killed, attenuated or inactivated bacteria, viruses, parasites or other microbes. Antibodies such as antiidiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein.

Further, for purposes of the present invention, antigens can be derived from any of several known viruses, bacteria, parasites and fungi, as well as any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response, may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A composition which contains a selected antigen adsorbed to a microparticle, displays "enhanced immunogenicity" when it possesses a greater capacity to elicit an immune response than the immune response elicited by an equivalent amount of the antigen when delivered without association with the microparticle. Thus, a composition may display "enhanced immunogenicity" because the antigen is more strongly immunogenic by virtue of adsorption to the microparticle, or because a lower dose of antigen is necessary to achieve an immune response in the subject to which it is administered. Such enhanced immunogenicity can be determined by administering the microparticle/antigen composition, and antigen controls to animals and comparing antibody titers against the two using standard assays such as radioimmunoassay and ELISAs, well known in the art.

The terms "effective amount" or "pharmaceutically effective amount" of a composition comprising microparticles with adsorbed macromolecules, as provided herein, refer to a nontoxic but sufficient amount of the microparticle/macromolecule composition to treat or diagnose a condition of interest. For example, these expressions may refer to an amount sufficient to provide a desired response, such as an immunological response, and corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual along with the microparticle formulation without causing any undesirable biological effects in the individual or interacting in a deleterious manner with any of the components of the composition in which it is contained.

The term "excipient" refers to substances that are commonly provided within finished dosage forms, and include vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, "treatment" (including variations thereof, for example, "treat" or "treated") refers to any of (i) the prevention of infection or reinfection, as in a traditional vaccine, (ii) the reduction or elimination of symptoms, and (iii) the substantial or complete elimination of the pathogen or disorder in question. Treatment may be effected prophylactically (prior to infection) or therapeutically (following infection).

As used herein, the phrase "nucleic acid" refers to DNA, RNA, or chimeras formed therefrom.

As used herein, the phrase "oligonucleotide comprising at least one CpG motif" refers to a polynucleotide comprising at least one CpG dinucleotide. Oligonucleotides comprising at least one CpG motif can comprise multiple CpG motifs. These oligonucleotides are also known as "CpG oligonucleotides" in the art. As used herein, the phrase "CpG motif" refers to a dinucleotide portion of an oligonucleotide which comprises a cytosine nucleotide followed by a guanosine nucleotide. 5-methylcytosine can also be used in place of cytosine.

As used herein, "alphavirus RNA vector replicon," "RNA vector replicon," "RNA vector construct," and "replicon" refer to an RNA molecule which is capable of directing its own amplification or self-replication in vivo, within a target cell. An alphavirus-derived RNA vector replicon should contain the following ordered elements: 5' viral sequences required in cis for replication (also referred to as 5' CSE), sequences which, when expressed, code for biologically active alphavirus nonstructural proteins (e.g., nsP1, nsP2, nsP3, nsP4), 3' viral sequences required in cis for replication (also referred to as 3' CSE), and a polyadenylate tract. An alphavirus-derived RNA vector replicon also may contain a viral subgenomic "junction region" promoter, sequences from one or more structural protein genes or portions thereof, extraneous nucleic acid molecule(s) which are of a size sufficient to allow production of viable virus, as well as heterologous sequence(s) to be expressed.

As used herein, "Eukaryotic Layered Vector Initiation System," "ELVIS," or "ELVIS vector" refers to an assembly which is capable of directing the expression of a sequence(s) or gene(s) of interest. The eukaryotic layered vector initiation system should contain a 5' promoter which is capable of initiating in vivo (i.e., within a cell) the synthesis of RNA from cDNA, and a viral vector sequence which is capable of directing its own replication in a eukaryotic cell and also expressing a heterologous sequence. In preferred embodiments, the nucleic acid vector sequence is an alphavirus-derived sequence and is comprised of a 5' sequence which is capable of initiating transcription of an alphavirus RNA (also referred to as 5' CSE), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE). In addition, the vector sequence may include a viral subgenomic "junction region" promoter, sequences from one or more structural protein genes or portions thereof, extraneous nucleic acid molecule(s) which are of a size sufficient to allow optimal amplification, a heterologous sequence to be expressed, one or more restriction sites for insertion of heterologous sequences, as well as a polyadenylation sequence. The eukaryotic layered vector initiation system may also contain splice recognition sequences, a catalytic ribozyme processing sequence, a nuclear export signal, and a transcription termination sequence.

"Alphavirus vector construct" refers to an assembly which is capable of directing the expression of a sequence or gene of interest. Such vector constructs are generally comprised of a 5' sequence which is capable of initiating transcription of an alphavirus RNA (also referred to as 5' CSE), as well as sequences which, when expressed, code for biologically active alphavirus nonstructural proteins (e.g., nsP1, nsP2, nsP3, nsP4), an alphavirus RNA polymerase recognition sequence (also referred to as 3' CSE), and a polyadenylate tract. In addition, the vector construct may include a viral subgenomic "junction region" promoter, sequences from one or more structural protein genes or portions thereof, extraneous nucleic acid molecule(s) which are of a size sufficient to allow production of viable virus, a 5' promoter which is capable of initiating the synthesis of viral RNA from cDNA in vitro or in vivo, a heterologous sequence to be expressed, and one or more restriction sites for insertion of heterologous sequences.

As used herein, the phrase "vector construct" generally refers to ELVIS vectors, which comprise the cDNA complement of RNA vector constructs, RNA vector constructs themselves, alphavirus vector constructs, and the like.

According to some embodiments of the present invention, compositions and methods are provided which treat, including prophylactically and/or therapeutically immunize, a host animal against viral, fungal, mycoplasma, bacterial, or protozoan infections, as well as to tumors. The methods of the present invention are useful for conferring prophylactic and/ or therapeutic immunity to a mammal, preferably a human.

The methods of the present invention can also be practiced on mammals, other than humans, including biomedical research applications.

B. GENERAL METHODS

The present inventors have found that adsorption of macromolecules to microparticles can be improved by ensuring that detergent is made available for forming a complex with the macromolecules at the time of adsorption. Further, a great variety of molecules, including charged and/or bulky macromolecules, can be adsorbed. Thus the microparticle/macromolecule compositions of the present invention can be used as a delivery system to deliver the biologically active components in order to treat, prevent and/or diagnose a wide variety of diseases.

The present invention can be used to deliver a wide variety of macromolecules including, but not limited to, pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, polynucleotides which encode therapeutic or immunogenic proteins, immunogenic proteins and epitopes thereof for use in vaccines, hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, enzymes, transcription or translation mediators, intermediates in metabolic pathways, immunomodulators, such as any of the various cytokines including interleukin-1, interleukin-2, interleukin-3, interleukin-4, and gamma-interferon, antigens, and adjuvants.

In a preferred embodiment the macromolecule is an antigen. A particular advantage of the present invention is the ability of the microparticles with adsorbed antigen to generate cell-mediated immune responses in a vertebrate subject. The ability of the antigen/microparticles of the present invention to elicit a cell-mediated immune response against a selected antigen provides a powerful tool against infection by a wide variety of pathogens. Accordingly, the antigen/microparticles of the present invention can be incorporated into vaccine compositions.

The effectiveness of the various uses of plasmid vectors and ELVIS vectors as described in the art may be enhanced by adsorbing selected plasmid and ELVIS vectors to microparticles with adsorbent surfaces, which facilitates introduction of the vector, and of heterologous nucleic acid sequences comprised in the vector, into the cells of an animal. Alternatively, RNA vector constructs may be adsorbed to the polymer microparticles or submicron emulsions of the invention for effective delivery of heterologous nucleic acid sequences into the cells of an animal. The commonly owned U.S. Provisional Patent Application filed on Sep. 28, 2000 (Ser. No. 60/236, 105) discloses the use of such polynucleotides adsorbed to certain microparticles. Thus, in a preferred embodiment, the macromolecule is a polynucleotide, such as a plasmid, an ELVIS vector, or an RNA vector construct. A particular advantage of the present invention is the ability of the microparticles with adsorbed ELVIS vector to generate cell-mediated immune responses in a vertebrate subject. Patent Application Serial No. 60/236,105 further describes the adsorption of polypeptide antigens, including HIV polypeptide antigens, to microparticles. The ability of the antigen/microparticles of the present invention to elicit a cell-mediated immune response against a selected antigen provides a powerful tool against infection by a wide variety of pathogens. Accordingly, the antigen/microparticles of the present invention can be incorporated into vaccine compositions.

Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any macromolecule for which cellular and/or humoral immune responses are desired, preferably antigens derived from viral pathogens that may induce antibodies, T-cell helper epitopes and T-cell cytotoxic epitopes. Such antigens include, but are not limited to, those encoded by human and animal viruses and can correspond to either structural or non-structural proteins.

The microparticles of the present invention are particularly useful for immunization against intracellular viruses which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69: 1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Patent Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed compositions and methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Bimaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 or gp140 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol and tat regions.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis*, *Neisseria meningitides* (A, B, C, Y), *Neisseria gonorrhoeae*, *Helicobacter pylori*, and *Haemophilus influenza*. Hemophilus influenza type B (HIB), *Helicobacter pylori*, and combinations thereof. Examples of antigens from *Neisseria meningitides* B are disclosed in the following co-owned patent applications: PCT/US99/09346; PCT IB98/01665; and PCT IB99/00103. Examples of parasitic antigens include those derived from organisms causing malaria and Lyme disease.

Additional antigens for use with the invention, some of which are also listed elsewhere in this application, include the following (references are listed immediately below):

A protein antigen from *N. meningitidis* serogroup B, such as those in Refs. 1 to 7 below.

an outer-membrane vesicle (OMV) preparation from *N. meningitidis* serogroup B, such as those disclosed in Refs. 8, 9, 10, 11 etc. below.

a saccharide antigen from *N. meningitidis* serogroup A, C, W135 and/or Y, such as the oligosaccharide disclosed in Ref. 12 below from serogroup C (see also Ref. 13).

a saccharide antigen from *Streptococcus pneumoniae* [e.g. Refs. 14, 15, 16].

an antigen from *N. gonorrhoeae* [e.g., Refs. 1, 2, 3].

an antigen from *Chlamydia pneumoniae* [e.g., Refs. 17, 18, 19, 20, 21, 22, 23].

an antigen from *Chlamydia trachomatis* [e.g. Ref. 24].

an antigen from hepatitis A virus, such as inactivated virus [e.g., Refs. 25, 26].

an antigen from hepatitis B virus, such as the surface and/or core antigens [e.g., Refs. 26, 27].

an antigen from hepatitis C virus [e.g. Ref. 28].

an antigen from *Bordetella pertussis*, such as pertussis holotoxin (PT) and filamentous haemaglutinin (FHA) from *B. pertussis*, optionally also in combination with pertactin and/or agglutinogens 2 and 3 [e.g., Refs. 29 & 30].

a diphtheria antigen, such as diphtheria toxoid [e.g., chapter 3 of Ref. 31] e.g. the $CRM_{197}$ mutant [e.g., Ref. 32].

a tetanus antigen, such as a tetanus toxoid [e.g., chapter 4 of Ref. 31].

a protein antigen from *Helicobacter pylori* such as CagA [e.g. Ref. 33], VacA [e.g. Ref. 33], NAP [e.g. Ref. 34], HopX [e.g. Ref. 35], HopY [e.g. Ref. 35] and/or urease.

a saccharide antigen from *Haemophilus influenzae* B [e.g. Ref. 13].

an antigen from *Porphyramonas gingivalis* [e.g. Ref. 36].

polio antigen(s) [e.g. Refs. 37, 38] such as IPV or OPV.

rabies antigen(s) [e.g. Ref. 39] such as lyophilized inactivated virus [e.g. Ref. 40, Rabavert™).

measles, mumps and/or rubella antigens [e.g., chapters 9, 10 and 11 of Ref. 31].

influenza antigen(s) [e.g. chapter 19 of Ref. 31], such as the haemagglutinin and/or neuraminidase surface proteins.

an antigen from *Moraxella catarrhalis* [e.g., time 41].

an antigen from *Streptococcus agalactiae* (Group B *streptococcus*) [e.g. Refs. 42, 43]

an antigen from *Streptococcus pyogenes* (Group A *streptococcus*) [e.g. Refs. 43, 44, 45].

an antigen from *Staphylococcus aureus* [e.g. Ref 46].

Compositions comprising one or more of these antigens.

Where a saccharide or carbohydrate antigen is used, it is preferably conjugated to a carrier protein in order to enhance immunogenicity [e.g. Refs. 47 to 56]. Preferred carrier proteins are bacterial toxins or toxoids, such as diphtheria or tetanus toxoids. The $CRM_{197}$ diphtheria toxoid is particularly preferred. Other suitable carrier proteins include *N. meningitidis* outer membrane protein [e.g. Ref. 57], synthetic peptides [e.g. Refs. 58, 59], heat shock proteins [e.g. Ref 60], pertussis proteins [e.g. Refs. 61, 62], protein D from *H. Influenzae* [e.g. Ref. 63], toxin A or B from *C. difficile* [e.g. Ref. 64], etc. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Saccharides from different serogroups of *N. meningitidis* may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or means [Ref. 30].

Where diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

It is readily apparent that the subject invention can be used to deliver a wide variety of macromolecules and hence to treat and/or diagnose a large number of diseases. In some embodiments, the macromolecule/microparticle compositions of the present invention can be used for site-specific targeted delivery. For example, intravenous administration of the macromolecule/microparticle compositions can be used for targeting the lung, liver, spleen, blood circulation, or bone marrow.

The adsorption of macromolecules to the surface of the adsorbent microparticles occurs via any bonding-interaction mechanism, including, but not limited to, ionic bonding, hydrogen bonding, covalent bonding, Van der Waals bonding, and bonding through hydrophilic/hydrophobic interactions. Those of ordinary skill in the art may readily select detergents appropriate for the type of macromolecule to be adsorbed.

For example, microparticles manufactured in the presence of charged detergents, such as anionic or cationic detergents, may yield microparticles with a surface having a net negative or a net positive charge, which can adsorb a wide variety of molecules. For example, microparticles manufactured with anionic detergents, such as sodium dodecyl sulfate (SDS), e.g., SDS-PLG microparticles, adsorb positively charged antigens, such as proteins. Similarly, microparticles manufactured with cationic detergents, such as CTAB, e.g., PLG/CTAB microparticles, adsorb negatively charged macromolecules, such as DNA. Where the macromolecules to be adsorbed have regions of positive and negative charge, either cationic or anionic or nonionic detergents may be appropriate.

Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include homopolymers, copolymers and polymer blends derived from the following: polyhydroxybutyric acid (also known as polyhydroxybutyrate); polyhydroxy valeric acid (also known as polyhydroxyvalerate); polyglycolic acid (PGA) (also known as polyglycolide): polylactic acid (PLA) (also known as polylactide); polydioxanone; polycaprolactone; polyorthoester; and polyanhydride. More preferred are poly($\alpha$-hydroxy acid), such as poly(L-lactide), poly(D,L-lactide) (both known as "PLA" herein), poly(hydoxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given use is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000.

If a copolymer such as PLG is used to form the microparticles, a variety of lactide:glycolide ratios will find use herein and the ratio is largely a matter of choice, depending in part on the coadministered macromolecule and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based, for example, on the nature of the antigen and disorder in question. Moreover, mixtures of microparticles with varying lactide:glycolide ratios will find use herein in order to achieve the desired release kinetics for a given macromolecule and to provide for both a primary and secondary immune response. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res*. (1988) 22:837-858.

The microparticles are prepared using any of several methods well known in the art. For example, in some embodiments, double emulsion/solvent evaporation techniques, such as those described in U.S. Pat. No. 3,523,907 and Ogawa et al., *Chem. Pharm. Bull*. (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying 2nd* Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst*. (1988) S(2):99-139; and ionic gelation as described by, e.g., Lim et al., *Science* (1980) 210:908-910.

In preferred embodiments, a water-in-oil-in-water (w/o/w) solvent evaporation system can be used to form the microparticles, along the lines described by O'Hagan et al., *Vaccine* (1993) 11:965-969, PCT/US99/17308 (WO 00/06123) to O'Hagan et al. and Jeffery et al., Pharm. Res. (1993) 10:362.

In general, the particular polymer is dissolved in an organic solvent, such as ethyl acetate, dimethylchloride (also called methylene chloride and dichloromethane), acetonitrile, acetone, chloroform, and the like. The polymer will be provided in about a 1-30%, preferably about a 2-15%, more preferably about a 3-10% and most preferably, about a 4-6% solution, in organic solvent. The polymer solution is then combined with an aqueous solution and emulsified to form an o/w emulsion. The aqueous solution can be, for example, deionized water, normal saline, or a buffered solution such as phosphate-buffered saline (PBS) or a sodium citrate/ethylenediaminetetraacetic acid (sodium citrate/ETDA) buffer solution. Preferably, the volume ratio of polymer solution to aqueous liquid ranges from about 5:1 to about 20:1, more preferably about 10:1. Emulsification is conducted using any equipment appropriate for this task, and is typically a high-shear device such as, e.g., an homogenizer.

A volume of the o/w emulsion is then preferably combined with a larger volume of an aqueous solution, which preferably contains a cationic, anionic, or nonionic detergent. The volume ratio of aqueous solution to o/w emulsion typically ranges from about 2:1 to 10:1, more typically about 4:1. Examples of anionic, cationic and nonionic detergents appropriate for the practice of the invention are listed above and include SDS, CTAB and PVA, respectively. Certain macromolecules may adsorb more readily to microparticles having a combination of detergents, for example, a combination of PVA and DOTAP. Moreover, in some instances, it may be desirable to add detergent to the above organic solution. Where a nonionic detergent such as PVA is used, it is typically provided in about a 2-15% solution, more typically about a 4-10% solution. Where a cationic or anionic detergent is used, it is typically provided in about a 0.05-5% solution, more typically about a 0.25-1% solution. Generally, a weight to weight detergent to polymer ratio in the range of from about 0.00001:1 to about 0.5:1 will be used, more preferably from about 0.0001:1 to about 0.5:1, more preferably from about 0.001:1 to about 0.5:1, and even more preferably from about 0.005:1 to about 0.5:1.

The mixture is then homogenized to produce a stable w/o/w double emulsion. Organic solvents are then evaporated. The formulation parameters can be manipulated to allow the preparation of small microparticles on the order of 0.05 µm (50 nm) to larger microparticles 50 µm or even larger. See, e.g., Jeffery et al., *Pharm. Res.* (1993) 10:362-368; McGee et al., *J. Microencap.* (1996). For example, reduced agitation results in larger microparticles, as does an increase in internal phase volume. Small particles are produced by low aqueous phase volumes with high concentrations of emulsion stabilizers.

A preferred apparatus for performing the above steps is schematically illustrated in FIG. 1. Referring now to FIG. 1, a manufacturing tank assembly, generally designated by the numeral 102, is shown. The tank assembly 102 is designed to be a "closed system," such that an aseptic environment is maintained during processing. All pieces of equipment and parts are preferably selected to be clean-in-place and autoclavable. All filters 104*a-d* are preferably fluoropolymer filters such as Super-Cheminert™ all-fluoropolymer filters from Pall Corporation. Initially, an aqueous solution, such as a sodium citrate/ETDA buffer system 106 and an organic polymer solution, such as a solution of PLG in methylene chloride 108, are filtered and fed into tank 110 where they are continuously mixed with mixer 112. The mixture is then fed through an in-line homogenizer 114 (e.g., a high speed, high shear autoclavable in-line homogenizer such as the Kinematica MT 5000), forming an o/w emulsion. The emulsion is cooled, for example by a water-cooled condenser 116, after emerging from the in-line homogenizer 114, whereupon it is returned to the tank 110. After the contents are emulsified to the desired extent, an aqueous detergent solution, for example a solution of CTAB in water 118, is added to the tank 110, whereupon a w/o/w emulsion is formed by again feeding the contents through the in-line mixer 114. After sufficient emulsification, the resulting w/o/w emulsion is purged with nitrogen via distributor 119 to remove the organic solvent. The nitrogen-laden solvent vapor is filtered and cooled in a condenser 120, capturing the solvent in container 122.

In embodiments where a relatively large weight to weight detergent to polymer ratio is used (e.g., detergent to polymer ratios of about 0.05:1 to about 0.5:1, more preferably about 0.10:1 to about 0.50:1, and most preferably about 0.2:1 to about 0.4:1), it is desirable to wash the particles to remove excessive amounts of detergent. Typically, this washing step is performed after the organic solvent is removed from the final emulsion, for example, by solvent evaporation (like that performed in connection with FIG. 1), by solvent extraction or both.

In some embodiments, the microparticles are washed by centrifugation. This process reduces the overall amount of detergent and leads to a final composition that contains relatively small amounts of unbound detergent relative to bound detergent. For instance, in Example 2 below, the washing steps that are performed (i.e., washing with water by centrifugation four times) yields microparticles having about 1% w/w CTAB, of which more than 99% is bound to the microparticles, and less than 1% is found in unbound form.

In other more preferred embodiments, the microparticles are subjected to a detergent-reducing process that nonetheless retains significant amounts of the detergent in unbound form. For instance, a cross-flow filtration step may be performed to retain a substantial amount of unbound detergent. Typically, a filtration step of this type yields microparticles containing about 0.2 to 5% w/w detergent overall, of which approximately 10 to 60% is bound to the microparticles, and approximately 40-90% is found in unbound form. More preferably, approximately 25 to 40% is bound to the microparticles, and approximately 60-75% is unbound. For instance, in the procedure described in Example 5 below, microparticles are produced having about 1% w/w CTAB overall, of which approximately 30% is bound to the microparticles, and approximately 70% is unbound.

In embodiments where a sufficiently small detergent to polymer ratio is used (e.g., detergent to polymer ratios of about 0.001:1 to 0.05:1, more preferably about 0.002:1 to about 0.04:1 and even more preferably about 0.006 to about 0.02:1, it is not necessary to wash the microparticles to remove excessive amounts of detergent. Typically, a process of this type yields microparticles having about 0.2 to 5% w/w detergent, of which approximately 10 to 60% is bound to the microparticles, and approximately 40-90% is found in unbound form. More preferably, approximately 25 to 40% is bound to the microparticles, and approximately 60-75% is found in unbound form. For instance, in the procedure described in Example 6 below, microparticles are produced having approximately 1% w/w CTAB, of which approximately 30% is bound to the microparticles, and approximately 70% is unbound.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM). Following preparation, microparticles can be stored as is or lyophilized for future use. In order to adsorb macromolecules to the microparticles, the microparticle preparation can be simply mixed with the macromolecule of interest and the resulting formulation can again be lyophilized prior to use. However, as noted above, the present inventors have found that adsorption of macromolecules to the polymer microparticles can be improved by ensuring that a substantial amount of detergent in unbound form is present at the time of macromolecule adsorption. In the case where very little of the detergent in the as-prepared microparticle composition is present in unbound form (e.g., approximately 5% or less), it is preferred to incubate the microparticles with both the macromolecule and an additional quantity of detergent. Preferably a weight to weight detergent to macromolecule ratio of about 0.002:1 to 0.05:1, more preferably about 0.005 to 0.02:1 is used.

On the other hand, where substantial amounts of the detergent in the as-prepared microparticle composition is present in unbound form (e.g., approximately 50-90% unbound, more preferably approximately 60-75%), good results can be achieved by simply incubating the microparticles with the macromolecule of interest, with the use of additional detergent being optional.

Without wishing to be bound by theory, in both of the above cases it is believed that unbound detergent is available to complex with the macromolecule of interest, rendering the macromolecule more amenable to adsorption to a microparticle.

Generally, macromolecules are added to the microparticles to yield microparticles with adsorbed macromolecules having a weight to weight ratio of from about 0.0001:1 to 0.25:1 macromolecules to microparticles, preferably, 0.001:1 to 0.1:1, more preferably 0.01:1 to 0.05:1. Macromolecule content of the microparticles can be determined using standard techniques.

The microparticles of the present invention may have macromolecules entrapped or encapsulated within them, as well as having macromolecules adsorbed thereon. Thus, for example, one of skill in the art may prepare in accordance with the invention microparticles having encapsulated adjuvants with proteins adsorbed thereon, or microparticles having encapsulated proteins with adjuvants adsorbed thereon. One of skill in the art may likewise prepare in accordance with the invention microparticles having encapsulated adjuvants with complexed ELVIS vectors adsorbed thereon, or microparticles having encapsulated antigen with nucleic acid plasmids adsorbed thereon. The invention contemplates a variety of combinations of complexed macromolecules adsorbed on and entrapped within microparticles, along with other macromolecules such as antigenic molecules.

Once the macromolecule-adsorbed microparticles are produced, they are formulated into pharmaceutical compositions, including vaccines, to treat and/or diagnose a wide variety of disorders, as described above. The compositions will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present in such vehicles. A biological buffer can be virtually any solution which is pharmacologically acceptable and which provides the formulation with the desired pH, i.e., a pH in the physiological range. Examples of buffer solutions include saline, phosphate buffered saline, Tris buffered saline, Hank's buffered saline, and the like. Other excipients known in the art can also be introduced into the final dosage form, including binders, disintegrants, fillers (diluents), lubricants, glidants (flow enhancers), compression aids, colors, sweeteners, preservatives, suspending/dispersing agents, film formers/coatings, flavors and printing inks.

Adjuvants may be used to enhance the effectiveness of the harmaceutical compositions. The adjuvants may be administered concurrently with the microparticles of the present invention, e.g., in the same composition or in separate compositions. Alternatively, an adjuvant may be administered prior or subsequent to the microparticle compositions of the present invention. In another embodiment, the adjuvant, such as an immunological adjuvant, may be encapsulated in the microparticle. Adjuvants, just as any macromolecules, may be encapsulated within the microparticles using any of the several methods known in the art. See, e.g., U.S. Pat. No. 3,523,907; Ogawa et al., *Chem Pharm. Bull.* (1988) 36:1095-1103; O'Hagan et al., *Vaccine* (1993) 11:965-969 and Jefferey et al., *Pharm. Res.* (1993) 10:362. Alternatively, adjuvants maybe adsorbed on the microparticle as described above for any macromolecule.

Immunological adjuvants include, but are not limited to: (1) aluminum alts (alum), such as aluminum hydroxide, aluminum phosphate, aluminum sulfate, etc.; (2) other oil-in water emulsion fonrulations (with or without other specific immunostimulating agents such as muramyl peptides (see below) or bacterial cell wall components), such as for example (a) MF59 (International Publication No. WO90/14837; Chapter 10 in *Vaccine design: the subunit an adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., Stimulon™ (Cambridge Bioscience, Worcester, Mass.)) may be used or particle generated therefrom such as ISCOMs (immunostimulating complexes), which ICOMS may be devoid of additional detergent e.g., WO00/07621; (4) Complete Freunds Adjuvant (CFA) and Incomplete Freunds Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (7) combinations of 3dMPL with, for example, QS21 and/or oil-in-water emulsions, e.g., EP-A-0835318, EP-A-0735898, EP-A-0761231; (8) oligonucleotides comprising CpG motifs (Roman et al., *Nat. Med.*, 1997, 3, 849-854; Weiner et al., *PNAS USA*, 1997, 94, 10833-10837; Davis et al., *J. Immunol.* 1988, 160, 870-876; Chu et al., *J. Exp. Med.*, 1997, 186, 1623-1631; Lipford et al., *Eur. J. Immunol.* 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883: Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-

5906; International patent applications WO96/02555, WO98/16247, WO98/18810, WO98/40100, WO98/55495, WO98/37919 and WO98/52581) i.e. containing at least one CG dinucleotide, with 5 methylcytosine optionally being used in place of cytosine; (9) a polyoxyethylene ether or a polyoxyethylene ester e.g. WO99/52549; (10) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (11) a saponin and an immunostimulatory oligonucleotide (e.g., a CpG oligonucleotide) (WO00/62800); (12) an immunostimulant and a particle of metal salt e.g. WO00/23105; (13) a saponin and an oil-in-water emulsion e.g. WO99/11241; (14) a saponin (e.g. QS21)+3dMPL+IL-12 (optionally+a sterol) e.g. WO98/57659; (15) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (16) other substances that act as immunostimulating agents to enhance the effectiveness of the composition. Alum (especially aluminum phosphate and/or hydroxide) and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of adjuvants, see *Vaccine Design, The Subunit and the Adjuvant Approach*, Powell, M. F. and Newman, M. J, eds., Plenum Press, 1995)

The compositions will comprise a "therapeutically effective amount" of the macromolecule of interest. That is, an amount of macromolecule/microparticle will be included in the compositions which will cause the subject to produce a sufficient response, in order to prevent, reduce, eliminate or diagnose symptoms. The exact amount necessary will vary, for example, depending on the subject being treated; the age and general condition of the subject to be treated; the severity of the condition being treated; in the case of an immunological response, the capacity of the subject's immune system to synthesize antibodies; the degree of protection desired and the particular antigen selected and its mode of administration, among other factors. An appropriate effective amount can be readily determined by one of skill in the art. Thus, a "therapeutically effective amount" will typically fall in a relatively broad range that can be determined through routine trials. For example, for purposes of the present invention, where the macromolecule is a polynucleotide, an effective dose will typically range from about 1 ng to about 1 mg, more preferably from about 10 ng to about 1 μg, and most preferably about 50 ng to about 500 ng of the macromolecule delivered per dose; where the macromolecule is an antigen, an effective dose will typically range from about 1 μg to about 100 mg, more preferably from about 10 μg to about 1 mg, and most preferably about 50 μg to about 500 μg of the macromolecule delivered per dose.

Once formulated, the compositions of the invention can be administered parenterally, e.g., by injection. The compositions can be injected either subcutaneously, intraperitoneally, intravenously or intramuscularly. Other modes of administration include nasal, mucosal, rectal, vaginal, oral and pulmonary administration, suppositories, and transdermal or transcutaneous applications.

Dosage treatment may be a single dose schedule or a multiple dose schedule. A multiple dose schedule is one in which a primary course of administration may be with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also, at least in part, be determined by the need of the subject and be dependent on the judgment of the practitioner.

Furthermore, if prevention of disease is desired, the macromolecules in vaccines, are generally administered prior to primary infection with the pathogen of interest. If treatment is desired, e.g., the reduction of symptoms or recurrences, the macromolecules are generally administered subsequent to primary infection.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Preparation of Blank Microparticles Using PVA

Blank microparticles (e.g., without adsorbed or entrapped macromolecules) were made using polyvinyl alcohol (PVA) as follows. Solutions used:
 (1) 6% RG 504 PLG (Boehringer Ingelheim) in dichloromethane.
 (2) 10% polyvinyl alcohol (PVA) (ICN) in water.

In particular, the microparticles were made by combining 10 ml of polymer solution with 1.0 ml of distilled water and homogenizing for 3 minutes using an Omni benchtop homogenizer with a 10 mm probe at 10K rpm to form a water/oil (w/o) emulsion. The w/o emulsion was added to 40 ml of the 10% PVA solution, and homogenized for 3 minutes, to form a water/oil/water (w/o/w) emulsion. The w/o/w emulsion was left stirring overnight for solvent evaporation, forming microparticles. The formed microparticles were washed with water by centrifugation 4 times, and lyophilized. The microparticles were then sized in a Malvern Master sizer for future use.

Example 2

Preparation of Blank Microparticles Using CTAB

Blank microparticles were produced using CTAB as follows. Solutions used:
 (1) 4% RG 504 PLG (Boehringer Ingelheim) in dimethyl chloride.
 (2) 0.5% CTAB (Sigma Chemical Co., St. Louis, Mo.) in water.

In particular, the microparticles were made by combining 12.5 ml of polymer solution with 1.25 ml of distilled water and homogenizing for 3 minutes using an Omni benchtop homogenizer with a 10 mm probe at 10K rpm to form a w/o emulsion. The w/o emulsion was added to 50 ml of the 0.5% CTAB solution and homogenized for 3 minutes to form a w/o/w emulsion. The w/o/w emulsion was left stirring overnight for solvent evaporation, forming microparticles. The formed microparticles were then filtered through a 38μ mesh, washed with water by centrifugation 4 times, and lyophilized. The microparticles were then sized in a Malvern Master sizer for future use.

Example 3

Preparation of Blank Microparticles Using SDS

Blank microparticles were produced using SDS as follows. Solutions used:
(1) 6% RG 504 PLG (Boehringer Ingelheim) in dimethyl chloride.
(2) 1% SDS (Sigma Chemical Co., St. Louis, Mo.) in water.

In particular, the microparticles were made by combining 12.5 ml of polymer solution with 50 ml of the SDS solution and homogenizing for 3 minutes using an Omni benchtop homogenizer with a 10 mm probe at 10K rpm. The emulsion was left stirring overnight for solvent evaporation. The formed microparticles were filtered through a 38μ mesh, washed with water by centrifugation 4 times, and lyophilized for future use. The microparticles were then sized in a Malvern Master sizer for future use.

Example 4

Microparticles with Adsorbed Complex of DNA/CTAB

Blank PLG/PVA microparticles were preformed using the standard solvent evaporation method. For a 1 gm batch size, 2 ml of deionized water (DI) was homogenized with 16 ml volume of a 6% w/v solution of RG 504 (PLG Polymer) in dichloromethane (DCM). This emulsion was homogenized for 2 minutes and to this mixture, 60 ml of a 10% w/v solution of polyvinyl alcohol (PVA) was added. The multiple emulsion was further homogenized for 3 minutes and then put on a magnetic stirrer for overnight solvent evaporation. The resultant microparticles were washed twice with deionized water and freeze dried. The microparticles were sized and were found to be around 1 um in size.

For preparing the DNA formulation, 100 mg of PLG/PVA microparticles were incubated with 1 mg of CTAB and 1 mg of DNA (pCMV-p55gag) in a 5 ml volume of TE buffer. The suspension was gently stirred overnight at 4 C for complete adsorption. The microparticles were-centrifuged once at 5000 rpm and the pellet washed once with 50 ml of TE buffer. The resultant pellet was suspended in 3 ml of DI water and the microparticles were freeze-dried.

The actual DNA adsorbed was estimated by both depletion (measurement of the supernatant) and base hydrolysis of the microparticles. The DNA load was found to be 0.91% w/w and the loading efficiency 91%.

10 mg of the formulation did not release any free DNA in vitro in 1 ml of TE buffer at day 1.

Example 5

Preparation of Blank Microparticles Using CTAB

Cross-flow Filtration Technique

Blank microparticles are produced using CTAB as follows. Solutions used: (1) 6% RG 504 PLG (Boehringer Ingelheim) in methylene chloride, (2) 0.5% CTAB (Sigma Chemical Co., St. Louis, Mo.) in water, (3) sodium citrate/EDTA in water. The microparticles are made in an apparatus like that illustrated in FIG. 1 by combining 80 ml of polymer solution with 10 ml of sodium citrate/EDTA solution in the tank with constant mixing. The mixture is then homogenized in the in-line homogenizer until an o/w emulsion with a disperse phase (water phase) having a mean particle size of 1-2 microns is achieved. At this point 310 ml CTAB solution is added to the tank with constant mixing. The mixture is then homogenized in the in-line homogenizer until a stable w/o/w emulsion with a disperse phase (o/w phase) having a mean particle size of 1-microns is achieved. The resulting w/o/w emulsion is purged with nitrogen to remove the organic solvent, and the as-formed microparticles are filtered using a 0.1 micron cross-flow filter cassette from Millipore, using a total of 4.0 liters of deionized water to remove excess CTAB. After final cross-flow filtration, the suspension is collected, which comprises approximately 1% CTAB, of which 30% is present in bound form and 70% is present in unbound form.

Example 6

Preparation of Blank Microparticles Using CTAB Non-washing Technique

Blank microparticles are produced using CTAB as follows. Solutions used: (1) 6% RG 504 PLG (Boehringer Ingelheim) in methylene chloride, (2) 0.01825% CTAB (Sigma Chemical Co., St. Louis, Mo.) in water, (3) sodium citrate/EDTA in water. The microparticles are made in an apparatus like that illustrated in FIG. 1 by combining 300 ml of polymer solution with 60 ml of sodium citrate/EDTA solution in the tank with constant mixing. The mixture is then homogenized in the in-line homogenizer until a o/w emulsion with a disperse phase (water phase) having a mean particle size of 1 micron is achieved. At this point 1.8 liters of CTAB solution are added to the tank with constant mixing. The mixture is then homogenized in the in-line homogenizer until a stable w/o/w emulsion with a disperse phase (o/w phase) having a mean particle size of 1 micron is achieved. The resulting w/o/w emulsion is purged with nitrogen to remove the organic solvent. The microparticle suspension is sized in a Malvern Master sizer for future use. These microparticles comprise approximately 1% CTAB, of which 30% is present in bound form and 70% is present in unbound form.

Example 7

Immunogenicity of Microparticles with Adsorbed p55 DNA

A DNA formulation is prepared by incubating 100 mg of the microparticle suspension (in a 10 ml volume) formed in Example 6 with 1.0 mg of DNA (a pCMVgag plasmid encoding HIV p55 gag protein under the control of the cytomegalovirus early promoter) in a 0.5 nl volume of Tris-EDTA buffer. The suspension is incubated at 4° C. for 12 hours. Following incubation, the DNA-loaded microparticles are centrifuged, washed with Tris-EDTA buffer, suspended in deionized water and freeze-dried (lyophilized). The DNA loading of the resulting microparticles is approximately 1% w/w.

The DNA-loaded microparticles are then injected intramuscularly in mice at two total DNA levels. DNA alone is also injected at the same two levels as a control. Each formulation is injected into ten mice. The mice were boosted after 28 days. Two weeks after the second immunization, serum is collected and the geometric mean titer (GMT) of each serum is measured, along with its standard error (SE). The results are summarized in the following table:

| Formulation | GMT | SE |
|---|---|---|
| PLG-CTAB p55 DNA (1% w/w load), 1 µg | 15,565 | 4,764 |
| PLG-CTAB p55 DNA (1% w/w load), 10 µg | 27,277 | 5,693 |
| 1 µg p55 DNA | 367 | 1,572 |
| 10 µg p55 DNA | 2,185 | 1,652 |

Although preferred embodiments of the subject invention have been described in some detail, it is understood that obvious variations can be made without departing from the spirit and the scope of the invention as defined by the appended claims.

REFERENCES

Ref. 1-International patent application WO099/24578.
Ref. 2-International patent application WO99/36544.
Ref. 3-International patent application WO99/57280.
Ref. 4-International patent application WO00/22430.
Ref. 5-Tettelin et al., (2000) *Science* 287:1809-1815.
Ref. 6-International patent application WO96/29412.
Ref. 7-Pizza el al. (2000) *Science* 287:1816-1820.
Ref. 8-International patent application PCT/IB01/00166.
Ref. 9-Bjune et al. (1991) *Lancet* 338(8775):1093-1096.
Ref. 10-Fukasawa et al. (1990) *Vaccine* 17:2951-2958.
Ref. 11-Rosenqvist et al. (1998) *Dev. Biol. Stand.* 92:323-333.
Ref. 12-Costantino et al. (1992) *Vaccine* 10:691-698.
Ref. 13-Costantino et al. (1999) *Vaccine* 17:1251-1263.
Ref. 14-Watson (2000) *Padiatr Infect Dis J* 19:331-332.
Ref. 15-Rubin (2000) *Pediatr Clin North Am* 47:269-285, v.
Ref. 16-Jedrzejas (2001) *Microbiol Mol Biol Rev* 65:187-207.
Ref. 17-International patent application filed on 3rd Jul. 2001 claiming priority from GB-0016363.4].
Ref. 18-Kalman et al. (1999) *Nature Genetics* 21:385-389.
Ref. 19-Read et al. (2000) *Nucleic Acids Res* 28:1397-406.
Ref. 20-Shirai et al. (2000) *J. Infect. Dis.* 181(Suppl 3):S524-S527.
Ref. 21-International patent application WO99/27105.
Ref. 22-International patent application WO00/27994.
Ref. 23-International patent application WO00/37494.
Ref. 24-International patent application WO99/28475.
Ref. 25-Bell (2000) *Pediatr Infect Dis J* 19:1187-1188.
Ref. 26-Iwarson (1995) *APMIS* 103:321-326.
Ref. 27-Gerlich et al. (1990) *Vaccine* 8 Suppl:S63-68 & 79-80.
Ref. 28-Hsu et al. (1999) *Clin Liver Dis* 3:901-915.
Ref. 29-Gustafsson et al. (1996) *N. Engl. J. Med.* 334:349-355.
Ref. 30-Rappuoli et al. (1991) *TIBTECH* 9:232-238.
Ref. 31-Vaccines (1988) eds. Plotkin & Mortimer. ISBN 0-7216-1946-0.
Ref. 32-Del Guidice et al. (1998) *Molecular Aspects of Medicine* 19:1-70.
Ref. 33-International patent application WO93/18150.
Ref. 34-International patent application WO99/53310.
Ref. 35-International patent application WO98/04702.
Ref. 36-Ross et al. (2001) *Vaccine* 19:4135-4142.
Ref. 37-Sutter et al. (2000) *Pediatr Clin North Am* 47:287-308.
Ref. 38-Zimmerman & Spann (1999) *Am Fam Physician* 59:113-118,125-126.
Ref. 39-Dreesen (1997) *Vaccine* 15 Suppl:S2-6.
Ref. 40-*MMWR Morb Mortal Wkly Rep* 1998 Jan. 16; 47(1): 12, 19.
Ref. 41-McMichael (2000) *Vaccine* 19 Suppl 1:S101-107.
Ref. 42-Schuchat (1999) *Lancet* 353(9146):51-6.
Ref. 43-GB patent applications 0026333.5, 0028727.6 & 0105640.7.
Ref. 44-Dale (1999) *Infect Dis Clin North Am* 13:227-43, viii.
Ref. 45-Ferretti et al. (2001) *PNAS USA* 98:4658-4663.
Ref. 46-Kuroda et al. (2001) *Lancet* 357(9264):1225-1240; see also pages 1218-1219.
Ref. 47-Ramsay et al. (2001) *Lancet* 357(9251):195-196.
Ref. 48-Lindberg (1999) *Vaccine* 17 Suppl 2:S28-36.
Ref. 49-Buttery & Moxon (2000) *J R Coll Physicians London* 34:163-168.
Ref. 50-Ahrnad & Chapnick (1999) *Infect Dis Clin North Am* 13:113-133, vii.
Ref. 51-Goldblatt (1998) *J. Med. Microbiol.* 47:563-567.
Ref. 52-European patent 0 477 508.
Ref. 53-U.S. Pat. No. 5,306,492.
Ref. 54-International patent application WO98/42721.
Ref. 55-*Conjugate Vaccines* (eds. Cruse et al.) ISBN 3805549326, particularly vol. 10:48-114.
Ref. 56-Hermanson (1996) *Bioconjugate Techniques* ISBN: 0123423368 & 012342335X.
Ref. 57-European patent application 0372501.
Ref. 58-European patent application 0378881.
Ref. 59-European patent application 0427347.
Ref. 60-International patent application WO93/17712.
Ref. 61-International patent application WO98/58668.
Ref. 62-European patent application 0471177.
Ref. 63-International patent application WO00/56360.
Ref. 64-International patent application WO00/61761.

We claim:

1. A method of producing a microparticle composition, said method comprising:
    (a) forming an emulsion comprising (i) a polymer selected from the group consisting of a poly($\alpha$-hydroxy acid), a polyhydroxy butyric acid, a polycaprolactone, a polyorthoester, a polyanhydride, and a polycyanoacrylate, (ii) an organic solvent, (iii) a detergent and (iv) water;
    (b) removing the organic solvent from the emulsion to form a microparticle suspension;
    (c) wherein said microparticle suspension is subjected to a filtration step to remove excess detergent such that about 10-90% of the total detergent in the resulting microparticle suspension is bound to the microparticles and the remainder is unbound, or wherein said microparticle suspension is not subjected to a step to remove excess detergent and the ratio of the detergent to the polymer used is such that about 10-90% of the total detergent in the microparticle suspension is bound to the microparticles and the remainder is unbound; and
    (d) mixing a biologically active macromolecule with said microparticle suspension in which about 10-90% of the total detergent in the microparticle suspension is bound to the microparticles and the remainder is unbound such that said biologically active macromolecule is adsorbed to microparticles in said suspension.

2. The method of claim 1, wherein the emulsion is a water-in-oil-in-water emulsion that is formed by a process comprising:
    (a) emulsifying an organic phase comprising the polymer and the organic solvent with a first aqueous phase comprising water to form a water-in-oil emulsion; and (b) emulsifying a second aqueous phase comprising the detergent and water with the emulsion formed in step (a) to form a water-in-oil-in-water emulsion.

3. The method of claim 1, wherein said microparticle suspension is subjected to a cross-flow filtration step.

4. The method of claim 1, wherein the polymer is a poly(D,L-lactide-co-glycolide) having a lactide/glycolide molar ratio ranging from 40:60 to 60:40 and a molecular weight ranging from 30,000 Daltons to 70,000 Daltons.

5. The method of claim 1, wherein about 10-60% of the total detergent in the microparticle suspension is bound to the microparticles and the remainder is unbound.

6. The method of claim 1, wherein about 25-40% of the total detergent in the microparticle suspension is bound to the microparticles and the remainder is unbound.

7. The method of claim 1, wherein said microparticle suspension is subjected to said filtration step.

8. The method of claim 1, wherein the microparticle suspension is not subjected to a step to remove excess detergent.

9. The method of claim 1, wherein said detergent comprises an anionic detergent.

10. The method of claim 9, wherein said biologically active macromolecule comprises a polypeptide.

11. The method of claim 1, wherein said detergent comprises a cationic detergent.

12. The method of claim 11, wherein said biologically active macromolecule comprises a polynucleotide.

13. A method of producing a microparticle composition, said method comprising:
 (a) forming an emulsion comprising (i) a polymer selected from the group consisting of a poly($\alpha$-hydroxy acid), a polyhydroxy butyric acid, a polycaprolactone, a polyorthoester, a polyanhydride, and a polycyanoacrylate, (ii) an organic solvent, (iii) a cationic detergent and (iv) water, wherein the cationic detergent is provided in the emulsion at a weight to weight detergent to polymer ratio of from about 0.05:1 to about 0.5:1;
 (b) removing the organic solvent from the emulsion to form a microparticle suspension;
 (c) subjecting said microparticle suspension to a filtration step to remove excess detergent such that about 10-90% of the total detergent in the resulting microparticle suspension is bound to the microparticles and the remainder is unbound; and
 (d) mixing a biologically active macromolecule with said microparticle suspension in which about 10-90% of the total detergent in the filtered microparticle suspension is bound to the microparticles and the remainder is unbound, such that said biologically active macromolecule is adsorbed to microparticles in said suspension.

14. The method of claim 13, wherein the cationic detergent is provided in the emulsion at a weight to weight detergent to polymer ratio of from about 0.1:1 to about 0.5:1, wherein the polymer is poly(D,L-lactide-co-glycolide), and wherein the cationic detergent is cetyl trimethyl ammonium bromide (CTAB).

15. The method of claim 13, wherein about 10-60% of the total detergent in the microparticle suspension is bound to the microparticles and the remainder is unbound.

16. The method of claim 13, wherein about 25-40% of the total detergent in the microparticle suspension is bound to the microparticles and the remainder is unbound.

17. The method of claim 13, wherein said biologically active macromolecule comprises a polynucleotide.

18. A method of producing a microparticle composition, said method comprising:
 (a) forming an emulsion comprising (i) a polymer selected from the group consisting of a poly($\alpha$-hydroxy acid), a polyhydroxy butyric acid, a polycaprolactone, a polyorthoester, a polyanhydride, and a polycyanoacrylate, (ii) an organic solvent, (iii) a cationic detergent and (iv) water, wherein the cationic detergent is provided in the emulsion at a weight to weight detergent to polymer ratio of from about 0.001:1 to about 0.05:1;
 (b) removing the organic solvent from the emulsion to form a microparticle suspension;
 (c) wherein said microparticle suspension is not subjected to a step to remove excess detergent and the ratio of the detergent to the polymer used is such that about 10-90% of the total detergent in the microparticle suspension is bound to the microparticles and the remainder is unbound; and
 (d) mixing a biologically active macromolecule with said microparticle suspension in which about 10-90% of the total detergent in the microparticle suspension is bound to the microparticles and the remainder is unbound, such that said biologically active macromolecule is adsorbed to microparticles in said suspension.

19. The method of claim 18, wherein the cationic detergent is provided in the emulsion at a weight to weight detergent to polymer ratio of from about 0.002:1 to about 0.04:1, wherein the cationic detergent is cetyl trimethyl ammonium bromide (CTAB), and wherein the polymer is poly(D,L-lactide-co-glycolide).

20. The method of claim 18, wherein about 10-60% of the total detergent in the microparticle suspension is bound to the microparticles and the remainder is unbound.

21. The method of claim 18, wherein about 25-40% of the total detergent in the microparticle suspension is bound to the microparticles and the remainder is unbound.

22. The method of claim 18, wherein said microparticle suspension is not subjected to a step to remove excess cationic detergent.

23. The method of claim 18, wherein said biologically active macromolecule comprises a polynucleotide.

* * * * *